United States Patent [19]
Gathani

[11] Patent Number: 5,392,795
[45] Date of Patent: Feb. 28, 1995

[54] DENTAL HYGIENE DEVICE

[76] Inventor: Naresh Gathani, 35 Derwent Gardens, Wembley, Middx. HA9 8SG, United Kingdom

[21] Appl. No.: 30,283

[22] PCT Filed: Oct. 2, 1991

[86] PCT No.: PCT/GB91/01701
§ 371 Date: Dec. 20, 1993
§ 102(e) Date: Dec. 20, 1993

[87] PCT Pub. No.: WO92/05722
PCT Pub. Date: Apr. 16, 1992

[30] Foreign Application Priority Data
Oct. 3, 1990 [GB] United Kingdom ............... 9021543

[51] Int. Cl.6 .............................................. A61C 15/00
[52] U.S. Cl. ..................... 132/323; 132/321
[58] Field of Search ............... 132/309, 321, 322, 323, 132/324, 327, 329

[56] References Cited
U.S. PATENT DOCUMENTS

| | | | |
|---|---|---|---|
| 4,304,245 | 12/1981 | Lichfield | 132/321 |
| 4,776,358 | 10/1988 | Lorch | 132/321 |
| 4,832,063 | 5/1989 | Smole | 132/321 |
| 4,836,226 | 6/1989 | Wolak | 132/321 |
| 5,125,834 | 6/1992 | Swan | 132/321 |

FOREIGN PATENT DOCUMENTS 118695 7/1944 Australia ........................... 132/321

Primary Examiner—Cary E. O'Connor
Attorney, Agent, or Firm—William E. Pelton

[57] ABSTRACT

A dental hygiene device for interstitial or interproximal cleaning comprising a handle (20) having spaced arms (21,22) and a reusable monofilament (23), which replaces the normal dental floss, stretched across the arms (21,22). The monofilament (23) may be hollow, have elastomeric properties and/or deliver therapeutic agents to the teeth. The tool may be built into the handle (31) of a toothbrush, with a filament fixed in place, for example, by integral molding, or detachably fixed in position. Several embodiments are disclosed, in one example the spaced arms may be movably hinged together.

8 Claims, 5 Drawing Sheets

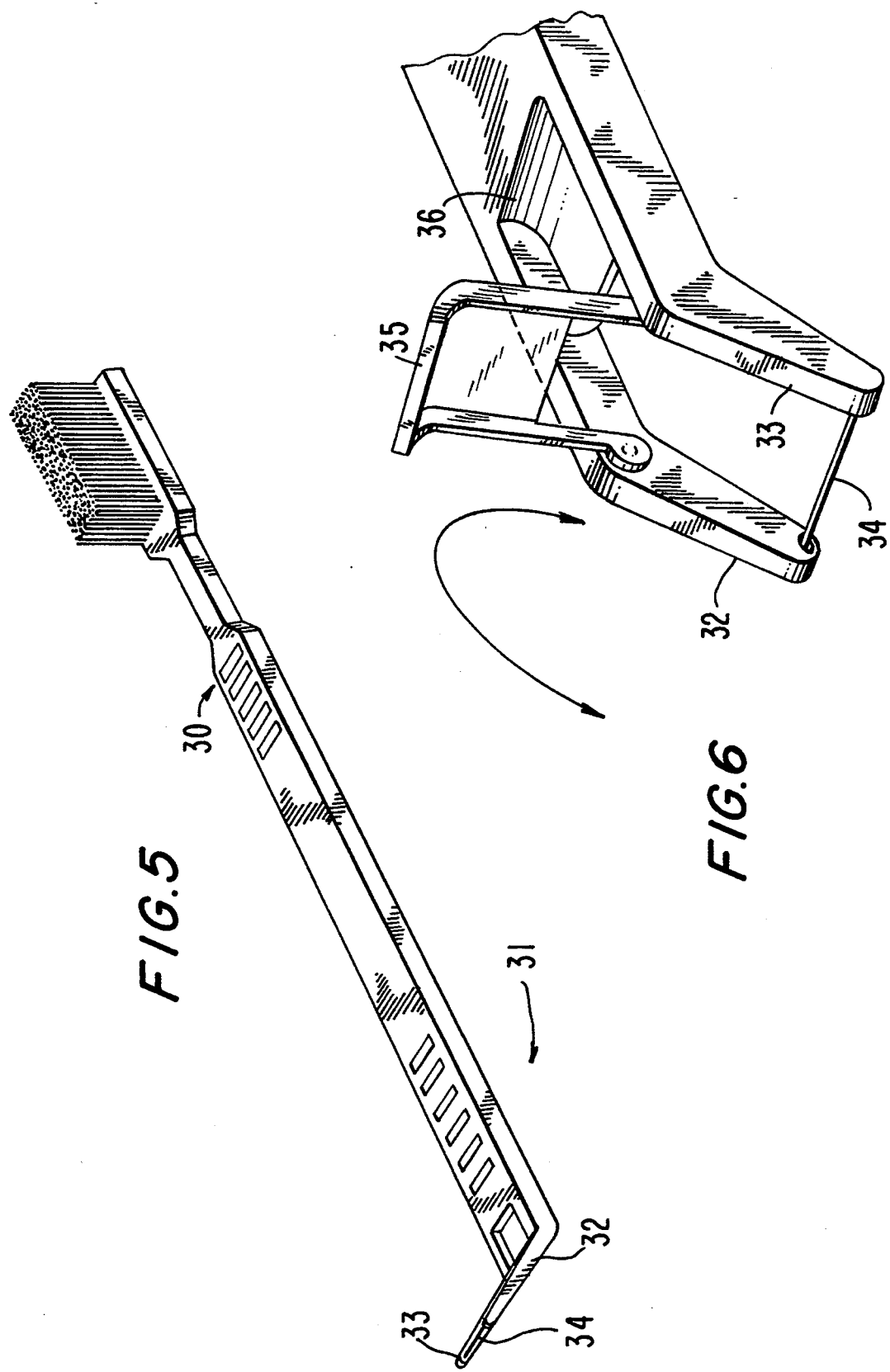

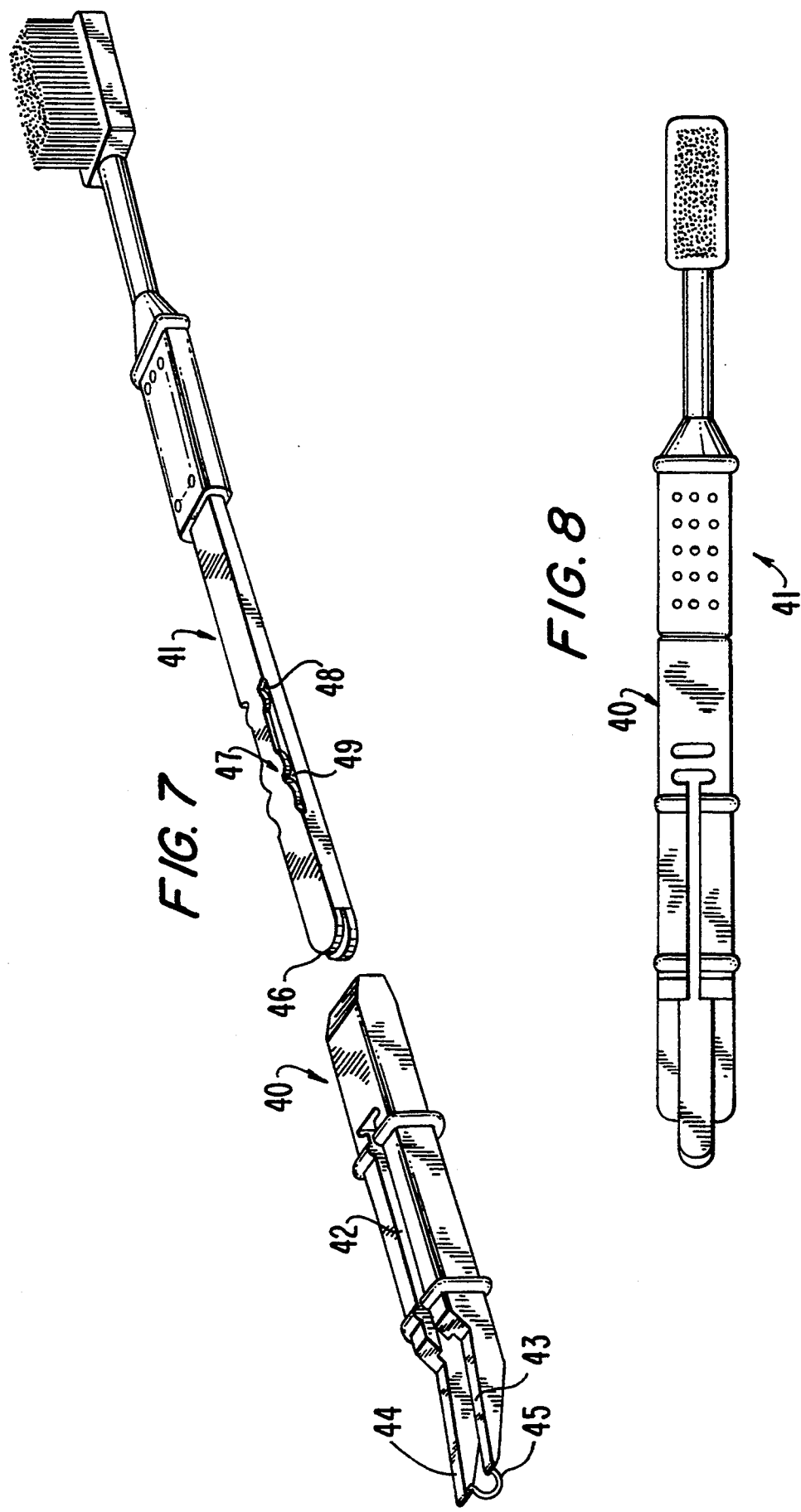

1

DENTAL HYGIENE DEVICE

The present invention concerns a dental hygiene device for interstitial cleaning.

It has been common practice for many years to use a material called dental floss for cleaning between teeth, apart from the use of a toothbrush for brushing them. Dental floss, as its name implies, is a filamentary material, like a fine thread, which is usually provided in a small dispenser which includes a cutter device. A user extracts a short length of floss, cuts it off, and then manipulates it using fingers to hold it taut to clean the interstitial spaces. Sometimes, a small tool can be used, having spaced arms, across which a length of floss can be tensioned.

Such a method of cleaning the interstitial spaces is generally awkward and less than satisfactory. The individual filaments of the floss tend to fray, and the floss traps material removed from between the teeth in among the fibres. Consequently, the floss can be used only once. The procedure also requires considerable time because of the need to cut a fresh length each time, and a manipulation of the thread by the fingers or the tool is generally inconvenient.

The invention aims to improve dental hygiene by facilitating interstitial cleaning in a number of ways, meeting some or all the above disadvantages.

Accordingly, the invention proposes a dental hygiene device for interstitial cleaning comprising a handle portion attached to spaced arm portions, and a filament stretched between said arm portions, characterised in that the filament is a hollow monofilament with continuous walls and capable of re-use.

A hygiene device as just described may be provided in a number of ways. At its simplest, the filament may be provided in a dispenser with a cutter, and a holder device for gripping a length of filament which, however, can be re-used so that it can be left ready for use whenever required without cutting fresh lengths. In an alternative, the device may be manufactured with a short length of filament fixed in place between the arm portions. Since the device can be moulded very cheaply, it can be used for a period of time and then thrown away.

In a preferred form, the device is integrated with a toothbrush. The handle of the toothbrush can be divided to form the arms of the device and a length of filament fixed in place. In a more sophisticated version, the handle portion and spaced arm portions can be formed by a sleeve member longitudinally slidable on the toothbrush handle between a retracted storage position and a projected use position. Relative movement of the sleeve member and the toothbrush handle into the projected position may cause spreading of the arm portions and tensioning of the filament.

In order that the invention may be clearly understood, various exemplary embodiments thereof will now be described with reference to the accompanying drawings in which:

FIG. 5 illustrates an adapted toothbrush which incorporates the dental hygiene device according to the invention;

FIG. 6 illustrates to an enlarged scale the device of FIG. 4;

FIG. 7 illustrates a further embodiment of the invention combined with a toothbrush;

FIGS. 8 and 9 show respectively a plan view and side view of the device in FIG. 7;

Figure 1:
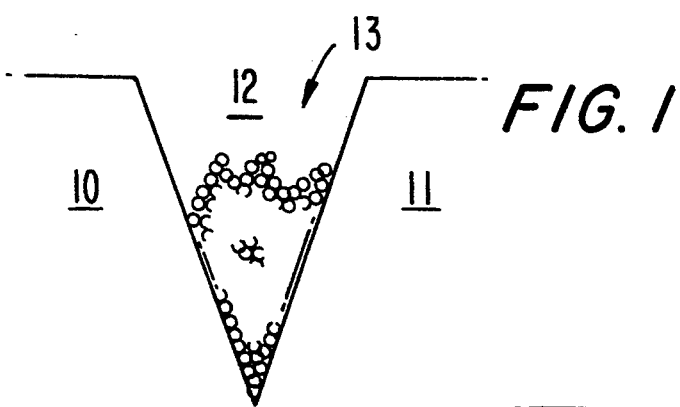
FIG. 1 illustrates in cross section the use of a conventional dental floss.

FIG. 1 is a diagrammatic view of two teeth 10,11 with an interstitial space 12. This is crudely shown as a V. Conventional dental floss 13 is illustrated in cross section, as it would be if inserted into the space for cleaning. Although individual strands of the floss 13 reach the very bottom of the space, it is clear that any undesired materials adhering to the sides of the teeth can become entrapped among the threads of the floss, rendering it usable only once since it cannot be cleaned. Moreover, it is easy for threads to become themselves trapped at the bottom of the V. Thus, although interstitial cleaning is very beneficial for maintaining healthy teeth, conventional dental floss suffers from disadvantages which discourage its frequent use. An additional reason for interstitial cleaning, particularly when carried out just after cleaning with a fluoride toothpaste, is that fluoride ions can be carried down into the interstitial spaces and deposited on the closely adjacent walls of the teeth. There is therefore a considerable incentive for making interstitial cleaning easier and more frequent.

Figure 2:
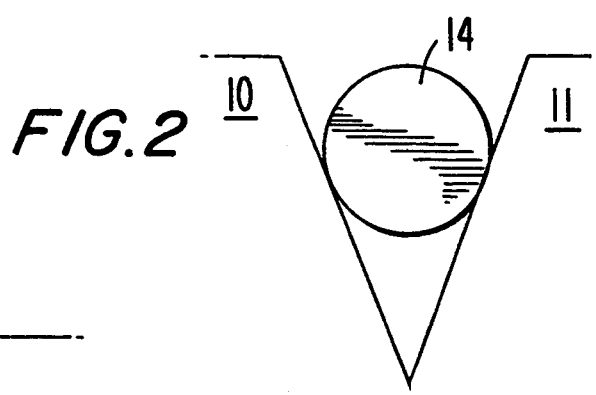
FIG. 2 illustrates the use of a solid monofilament.
Figure 3:
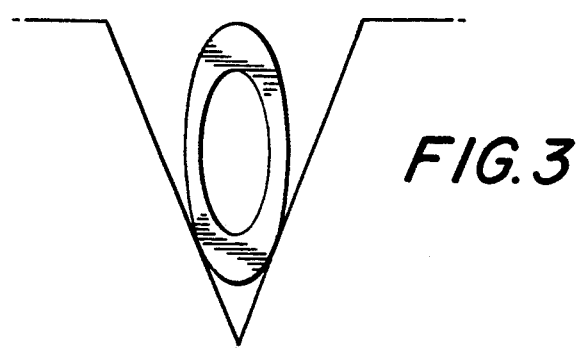
FIG. 3 illustrates the use of a hollow monofilament.

The invention therefore proposes the solution shown in FIG. 3. In this case, a monofilament 14 is used which is hollow. Naturally, a solid filament such as shown FIG. 2 will not penetrate to the very bottom of a V-shaped space, but in reality the interstitial space does not usually terminate in the manner illustrated, but has the form of a continuous gap which narrows in the middle. Consequently, it is necessary to choose a filament thickness which is great enough to provide sufficient strength but narrow enough to pass through the average interstitial space of human teeth. A thickness may be chosen in the range 0.1 mm to 1.0 mm in diameter. Suitable materials might be nylon or an elastomeric material.

From FIG. 3, it will be seen that a hollow filament (in this case circular but squashed into the gap) has a number of advantages. Because of its compressibility, it can get further into narrow gaps and it is also likely to have greater longitudinal elasticity.

Both the filaments in FIGS. 2 and 3 remain relatively clean, and do not absorb water significantly. Nor do they shred easily. As a consequence, they meet the criteria for reusability.

Such a hollow filament is, however, relatively expensive compared with a multifilament floss if the former is to have the necessary Strength and resistance to wear and shredding. Consequently, it must be re-used and cannot in practice therefore be used without a tool. As previously explained, its use with a tool would represent one of the major advantages of the invention.

Figure 4:
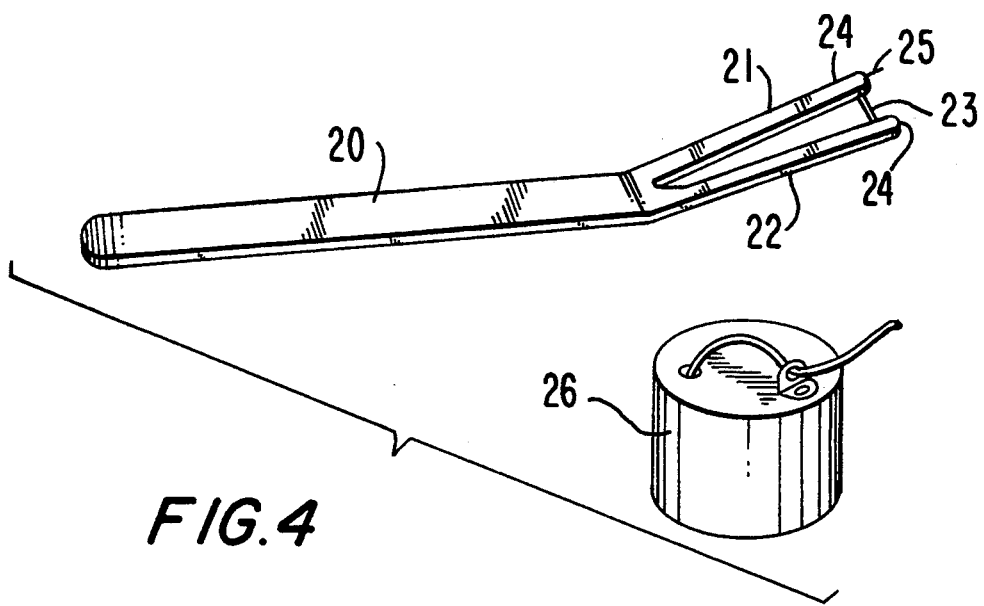
FIG. 4 illustrates a simple form of dental hygiene device according to the invention.

A simple tool is illustrated in FIG. 4. This comprises a handle portion 20 rigidly connected to a pair of splayed arm portions 21, 22. The arm portions are additionally bent, out of the plane of the handle portion by about 20°, but might be up to 45°. A short length of filament 23 as described with reference to FIG. 2 or FIG. 3 is firmly connected between the ends 24 of the arm portions. The filament may be attached by any suitable means. If the whole device is moulded from plastics, then the filament might be moulded in place ab initio, or welded by ultrasonic welding afterwards. In the latter case, the arms 21,22 are preferably forced inwards as the welding is performed, so that they spring outwards to tension the filament 23 when released.

Such a tool has the advantage of simplicity and cheapness. The angling of the arms provides an ergonomically satisfactory shape which makes the tool easy to manipulate in use in the mouth, even to reach the molars.

In an alternative, such a straightforward plastic tool may be provided without a filament 23 fitted, but with suitable mechanical means for engaging and holding a short length of filament cut by a user from a supply reel. The means for holding a filament might comprise small slots in the ends 24 of the arms into which the filament may be wedged so as to hold it tight. The slots would preferably not be aligned, but could indeed lie parallel to each other along the respective arm portions as indicted by dotted line 25. The filament would be provided in a small dispenser, 26 including preferably a cutter device, so that a user could replace the filament with a fresh short length whenever desired.

FIGS. 5 and 6 illustrate a toothbrush modified at the end furthest from the head to form a dental hygiene device according to the invention. An otherwise conventional toothbrush 30 is widened at the handle end 31 furthest from time bristles and forked to provide arm portions 32,33. Across the extremities of the arm portions, a filament 34 is fixed. This may be covered by a protector 35 which may be folded back into a recess 36 when the device is in use. Such a device has the obvious advantages that it is ready to hand when cleaning ones teeth, and the cost can be minimised since marketing and production of the toothbrush and the hygiene device are carried out together, thus reducing the cost. There is the further advantage that if the hygiene device is used immediately after the teeth have been cleaned using a fluoride toothpaste, the device is able to transfer the fluoride ions which are in the mouth from the toothpaste into the interstitial spaces and deposit them on the tooth surfaces. This assists in the prevention of tooth disease.

Figure 9:
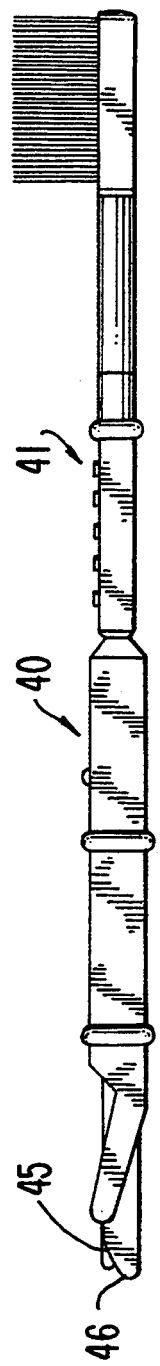

FIGS. 7,8 and 9 illustrate a different version of a combined toothbrush and dental hygiene device. In this case, the handle of the toothbrush serves as a support for a sleeve member 40 which slides over the handle 41 of the toothbrush. The sleeve member 40 is divided by a slot 42 to form two arm portions 43,44 and a filament 45 is fixed between the extremities of the arm portions. However, in this case, the filament 45 does not have to be held permanently taut, since the construction is such that the arms 43,44 can be spread outwards to create sufficient tension in the filament. FIGS. 8 and 9 illustrate the sleeve member in its retracted storage position in which the filament is slack and comes to rest for protection purposes in a recess 46 at the end of the handle 41.

The sleeve member is retained in its retracted position, and also in a series of projected positions (not illustrated) by moulded formations 47 on the handle 41 of the toothbrush and corresponding projections (not shown) within the sleeve member 40 which together form a ratchet. The formations 47 consist of a series of shoulders which inter-engage with the projections in the sleeve member. The end shoulder 48 retains the sleeve member in the retracted position, while the subsequent shoulders 49 cause progressive spreading of the arm portions 43,44, thus introducing suitable tension into the filament 45 and ensuring that the slot 42 close to the filament is wide enough for the device to straddle the teeth. A filament length in use of about 14 mm is desirable.

Figure 10:
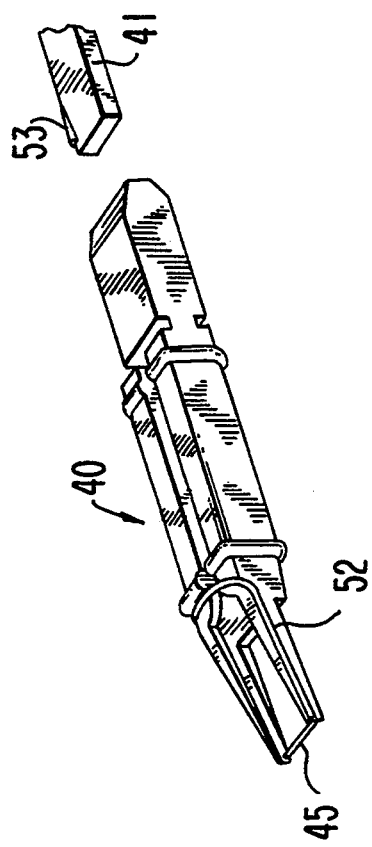
FIG. 10 illustrates a slightly modified version of the device in FIG. 7.

In a modified version illustrated in FIG. 10, the filament 45 need not be fixed e.g. by welding, to the arms of the sleeve member, but may form a small continuous loop 52 which extends back along the sleeve member and is engaged in suitable channels which maintain it in position. In case such a loop became trapped between a user's teeth, a cutter device 53 with a sharp top edge could be incorporated on the toothbrush handle 41 which, in a yet further extreme position, would sever the loop to detach it from the sleeve member and allow it to be pulled out sideways from the interstitial space.

In the versions of the device in FIGS. 7 to 10, it is envisaged that the filament will have a life equal to the expected life of a toothbrush, namely up to three months.

Figure 11:
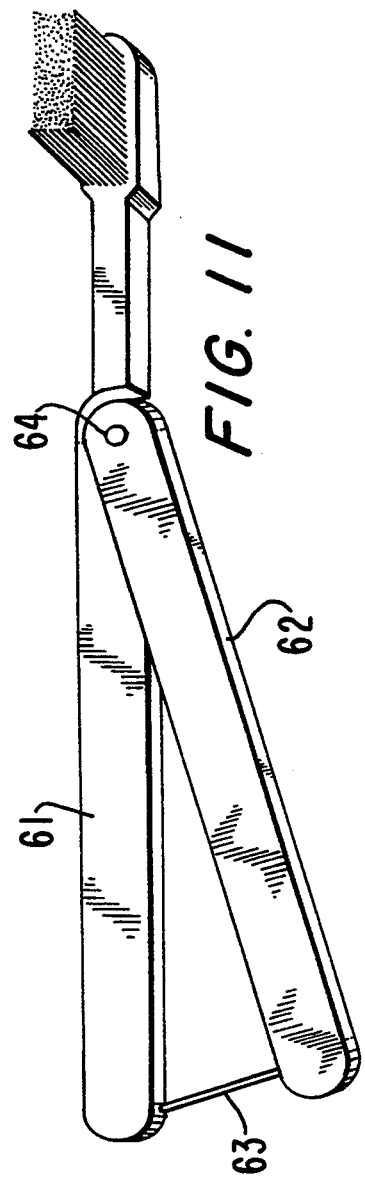
FIGS. 11 and 12 illustrate another embodiment of the invention combined with a toothbrush.
Figure 12:
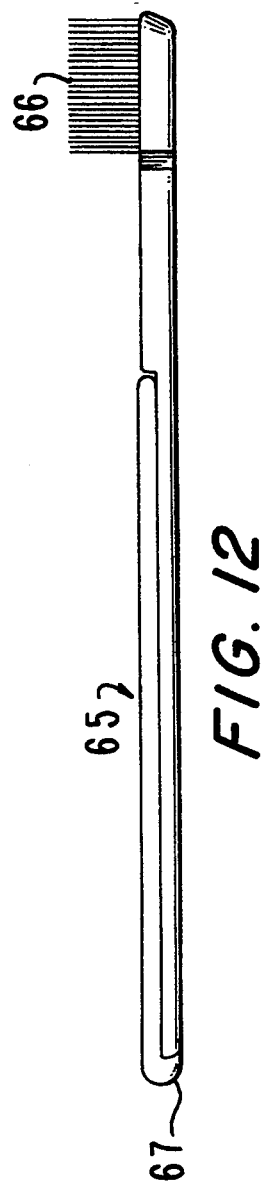

The embodiment shown in FIGS. 11 and 12 comprises a toothbrush comprising a head 66 and a handle portion 65. An arm portion 62 is hinged to the handle portion by a rotation joint 64 situated near the head. A filament 63 is stretched between the arm portion and the handle portion. The arm portion and the handle portion can be moved together in a scissor action.

The arm portion 62 has a constant thickness along all of its length, apart from a thickened portion 67 at the end remote from the rotation joint 64. The handle portion 65 is formed with the end adjacent to the head 66 thicker than the other end 61. The handle portion is stepped adjacent to the rotation joint 64.

FIG. 11 shows the device ready for use for interstitial cleansing. The arm portion 62 and the handle portion 65 are held so that the filament 63 is taut and ready for use, conveniently by interengaging formations on respective portions.

The handle portion 65 and the arm portion 62 are formed so that they can overlap each other (FIG. 12). This allows the arm member to form a continuous handle body with the handle portion. In this position the toothbrush can be used in a conventional manner.

The filament 63 is reusable, hollow and is rigidly and permanently attached between the inside edges of the handle portion 65 and the arm member 62. This arrangement allows interstitial cleansing.

In a modification to this embodiment of the invention the filament 63 can have elastomeric properties. The filament can deliver Fluoride ions or antibacterial agents from a suitable dentifice to the interstitial surfaces.

I claim:

1. A dental hygiene device for interstitial cleaning comprising a handle portion (20) attached to spaced arm portions, and a filament stretched (23) between said arm portions, characterised in that the filament is a hollow monofilament with continuous walls and capable of re-use.

2. A dental hygiene device according to claim 1, in the form of a kit comprising a filament dispenser incorporating a cutter device for severing lengths of the filament, the arm portions of the device being formed by a generally Y-shaped holder with means at each extremity for gripping one end of a length of the filament.

3. A dental hygiene device according to claim 1, wherein the handle portion (31) is formed by the handle of a toothbrush and the arm portions (32,33) are formed by longitudinal division of the handle.

4. A dental hygiene device as claimed in claim 3, wherein the filament (34) is rigidly fixed to the ends of the arms.

5. A dental hygiene device as claimed in claim 3, wherein the filament (52) is in the form of a closed loop, one portion (45) of which stretches across the ends of the arms (43,44).

6. A dental hygiene device as claimed in claim 1, which is incorporated in the handle (41) of a toothbrush, wherein said handle portion and spaced arm portions (43,44) of the device are formed by a sleeve member (40) longitudinally slidable on said toothbrush handle between a retracted storage position and a projected use position.

7. A dental hygiene device as claimed in claim 6, wherein the toothbrush handle (41) comprises molded shoulder formations which engage with said sleeve member upon longitudinal sliding of said sleeve member (40) and said toothbrush handle (41), causing spreading of the arm portions (43, 44) and tensioning of the filament (45) in the projected use position.

8. A dental hygiene device as claimed in claim 1, wherein the arm portions (61,62) are hinged together at one end.

* * * * *